United States Patent
Los

(10) Patent No.: US 8,685,449 B2
(45) Date of Patent: Apr. 1, 2014

(54) PHARMACEUTICAL COMPOSITION WITH ANTI-OBESITY ACTIVITY COMPRISING A PREMIXTURE OF PURE ORLISTAT AND PREPARATION PROCESS

(75) Inventor: Mario Atilio Los, Buenos Aires (AR)

(73) Assignees: Laboratorios Bago S.A., Buenos Aires (AR); Eastbrand Holding GmbH, Vienna (AT)

( * ) Notice: Subject to any disclaimer, the term of this patent is extended or adjusted under 35 U.S.C. 154(b) by 0 days.

(21) Appl. No.: 13/576,606

(22) PCT Filed: Feb. 1, 2010

(86) PCT No.: PCT/EP2010/000579
§ 371 (c)(1),
(2), (4) Date: Aug. 1, 2012

(87) PCT Pub. No.: WO2011/091816
PCT Pub. Date: Aug. 4, 2011

(65) Prior Publication Data
US 2012/0294941 A1    Nov. 22, 2012

(51) Int. Cl.
*A61K 9/44* (2006.01)

(52) U.S. Cl.
USPC .......................................................... 424/467

(58) Field of Classification Search
None
See application file for complete search history.

(56) References Cited

U.S. PATENT DOCUMENTS 6,004,996 A    12/1999    Shah et al.
2006/0246141 A1    11/2006    Liversidge et al.

FOREIGN PATENT DOCUMENTS

WO    WO-2009/116880 A2    3/2009
WO    WO-2009/044380 A2    4/2009
WO    WO2009044380 A2 *    4/2009

* cited by examiner

*Primary Examiner* — Anand Desai
*Assistant Examiner* — Melissa Mercier
(74) *Attorney, Agent, or Firm* — Gifford, Krass, Sprinkle, Anderson & Citkowski, P.C.

(57) ABSTRACT

Pharmaceutical compositions with anti-obesity activity that act peripherally are provided, which comprise a premixture made up of pure orlistat as the active ingredient and other components that afford the premixture stability and suitable physical properties for simply preparing compositions for oral use with convenient dosage flexibility; and optionally necessary thickening, flavouring and colouring agents. A method for preparing said compositions is also provided. The orlistat content in the premixture is less than 20% of the total weight of the mass, preferably between 12 and 17%.

The pharmaceutical composition can be formulated indistinctively from the premixture both as grooved tablets and powder for suspension.

19 Claims, No Drawings

PHARMACEUTICAL COMPOSITION WITH ANTI-OBESITY ACTIVITY COMPRISING A PREMIXTURE OF PURE ORLISTAT AND PREPARATION PROCESS

REFERENCE TO RELATED APPLICATION

This application is a 371 application of PCT/EP2010/000579, filed Feb. 1, 2010, the entire content of which is incorporated herein in its entirety.

TECHNICAL FIELD OF THE INVENTION

This invention relates to pharmaceutical compositions with anti-obesity activity that act peripherically and comprise a premixture made up of pure orlistat as the active ingredient and other components which afford the premixture stability and suitable physical properties for the simple preparation of oral compositions with convenient dosage flexibility; and necessary thickening, flavouring and colouring agents. The invention also relates to a method for preparing said compositions.

BACKGROUND

Approximately a third of Americans between 20 and 70 years old are considered obese and approximately half of the American population in this age category are considered to be overweight. Obesity is also considered to be an increasing problem in other industrialised countries and in emergent countries where a large amount of people are used to calorie-rich diets influenced by the West. It has been estimated that obesity contributes to up to 50% of chronic diseases in western societies, and is responsible for approximately el 70% of foreseeable deaths in the United States.

Obesity and the disorders it causes, pose serious health problems that are frequent in the United States and throughout the world. Obesity of the abdominal part of the body is the most important known risk factor of Type 2 mellitus diabetes, and represents an important risk factor in cardiovascular diseaeses. Obesity is a recognised risk factor for hypertension, arteriosclerosis, congestive cardiac insufficiency, cerebrovascular accident, cholecystitis, osteoarthritis, sleep apnea syndrome, reproduction disorders such as polycystic ovarian syndrome, breast, prostate and colon cancer, and it is also a recognised risk factor or greater incidences of general anaesthetia complications. Also, it includes a serious risk of comorbility because of the affections described above and for alterations such as infections, varicose veins, Acantosis nigricans, eczemas, exercise intolerance, insulin resistance, hypertension, hypercholesterolemia, gallstones, orthopedic injuries and thromboembolic diseases. Obesity is also a risk factor of the group of diseases called "insulin resistance syndrome" or "X syndrome".

The medical care costs associated with obesity are substantial. As a result of these factors, the development of compositions for managing to lose weight is a subject of significant commercial interest.

Some weight control approaches include appetite suppressors, reduced calorie diets, exercise programmes, surgical procedures and the like. A variety of weight controlling compositions have been developed; the desired characteristics for these products include the lack of undesirable side effects, high efficiency, convenient dosage rates, and low cost. The drugs developed for treating obesity can have undesirable side effects, are only be available under medical supervision, and can be relatively expensive. Other products such as those with a high fibre content can require large inconvenient doses in order to be effective.

One method of inhibiting the digestion and/or metabolism of lipids in the diet has been to administer non-absorbible materials that are apt for joining up with the lipds or kidnapping them. Another approach to inhibiting digestion and/or the metabolism of dietic lipids is to use compounds that inhibit the activity of certain enzymes that are necessary for lipid digestion. Polymers that inhibit the action of pancreatic lipase are described in U.S. Pat. No. 3,923,976.

Other lipase inhibitors include lipstatin and orlistat. The latter is also known as (–) tetrahydrolipstatin or THL, and it is a derivative of a natural product excreted by Streptomyces toxytricini. It has been discovered that this class of compounds have both in vitro and in vivo activity against various lipases, such as lingual lipase, pancreatic lipase, gastric lipase, and carboxyl ester lipase.

The (–) tetrahydrolipstatin or orlistat (96829-58-2) defined as an inhibitor of the pancreatic lipase and anti-obesity agent (Merck Index XIII Edition) has been mentioned in several patents, including, European patent EP 129 748 (U.S. Pat. No. 4,598,089/1986) granted in the name of Hoffman La Roche, equivalent to Argentinian patent No AR 233.709; U.S. Pat. No. 6,004,996 equivalent to Argentinan patent AR 10.704 B2; and others.

The therapeutic effect of orlistat occurs in the gastric cavity and in the small intestine through the formation of a covalent link in the active site of the serine in gastric and pancreatic lipases, which blocks the hydrolisis of the easily absorbible fats or free fatty acids and monoglycerides.

It has been proved that the absorption of orlistat is minimum, and that the effect is local and non-systemic.

A dosis of 120 mg of orlistat with every main meal, including breakfast, has been recommended.

It has also been recommended to associate it with a diet that provides less than 30% of the total calories originating from fats, in order to reduce the adverse gastro-intestinal effects.

The adverse gastro-intestinal effects observed are associated with the capacity of the (–) tetrahydrolipstatin to prevent the absorption of fats. These particularly include: fat excrement and fecal incontinence associated with the fat content intake.

Such secondary effects frequently lead to the patient suspending the treatment. Particularly when the pharmaceutical form cannot be fractioned and the doctor is inhibited to offer another more flexible alternative dosis.

Since the discovery of orlistat, there has only been one oral pharmaceutical form, i.e.: capsules, and one commercial concentration of 120 mg available for its therapeutical application in human medicine. During 2007, the FDA authorised the first pharmaceutical product also in capsules, with its composition including 60 mg of orlistat, and it represents an important advance in flexibilising the dosis that each patient needs according to their situation and eating habits. In 2009, orlistat 60 mg in capsules was also authorised as OTC products.

Producing oral pharmaceutical forms that comprise orlistat in the form of pellets has proved to not be easy, and this is highlighted in technical literature. Only capsules containing 120 or 60 mg of orlistat exist. This circumstance can also limit the dosage flexibility that certain patients may need.

Technically the literature mentions some features of (−) tetrahydrolipstatin that create practical disadvantages for preparing other oral pharmaceutical forms:

a) (−) Tetrahydrolipstatin is a substance that has a low melting point: 43° C. (Index Merck XIII Edition).
b) It is susceptible to hydrolisis and thermal degradation. Particularly in a wet environment and at a temperature above 35° C., and inclusive in a dry environment (U.S. Pat. No. 6,004,996).
c) Document U.S. Pat. No. 6,004,996 highlights that tablets or capsules cannot be formed easily using the conventional wet granulating method because of adhesion problems during the preparation of the tablet or during encapsulation.

Consequently, the technical solutions have been aimed preferably at specifically preparing capsules. U.S. Pat. No. 6,004,996 describes the preparation of granules or pellets containing orlistat, together with other acceptable ingredients for obtaining particules between 0.25 and 2 mm that are useful for preparing capsules.

The described alternatives make it possible to overcome the problem of the stability of orlistat. However, the following is observed:

i) obtaining pellets using the method described in document U.S. Pat. No. 6,004,996 requires 7 operations and a drying stage on a fluid bed (Aeromatic MP-I) with an air inlet at a temperature that must be below 35° C.
ii) it only allows a single dosis capsule type pharmaceutical composition to be prepared, with a low dosage flexibility for the patient and the prescribing doctor.
iii) preparing the pellets involves an industrial method that implies using various pieces of specific equipment that are different from those normally used for preparing pharmaceutical forms.
iv) since preparing pellets requires various stages and special equipment, it incurrs an extra cost in addition to the industrial preparation of the pharmaceutical form.

Another approach to trying to reduce the drawbacks of the art is described in U.S. Pat. No. 6,703,369 (Sep. 3, 2004) granted to Hoffmann La Roche (equivalent to Argentinian application AR 025 609 A1 (Apr. 12, 2002)), wherein a pharmaceutical composition is provided that comprises orlistat and at least one polyol fatty acid ester that has a melting point above 37° C. and wherein the fatty acid has twelve or more atoms.

The composition comprises at least one heavy acid ester of a polyalcohol corresponding to the group Trilaurin (PF 46-47° C.), Trimyristin (PF 56-57° C.), Tripalmitin (PF 68° C.), Triestearin (PF 71-73° C.), or a monoglyceride such as Monolaurin (PF 63° C.), Monomyristin (PF 69-70° C.), Monopalmitin (PF 63-68° C.).

Owing to the nature of the components mentioned, the preparation of the compositions claimed requires, where appropriate, the following type of operations:

Heating to 57-63° C.
Cooling subsequently to room temperature.
Heating to 39° C. up to 4 hours
Operating in an inert environment.
Cold grinding using dry ice or nitrogen (at −80° C.)

In other words, several stages require high temperatures over 50° C. However, according to the literature the contents disclosed by the same authors of this patent, orlistat undergoes hydrolitic and thermal degrading, over de 35° C. (U.S. Pat. No. 6,004,996; Stalder Henri, Schneider Pierre, Gottfried Oesterhelt; "Tetrahydrolipstatin: Thermal and Hydrolytic Degradation", Helvetica Chimica Acta; 73 (1990); pages 1022-1035).

Therefore, there is still the need to prepare a pharmaceutical composition for treating obesity, whereby it it possible to regulate the administration dosis of orlistat and which also is prepared by a simple and economic method without generating losses through degradation of the active orlistat compound.

SUMMARY OF THE INVENTION

The main aim of this invention is to provide a premixture with pure orlistat (not pellets) as the active ingredient and other components that make it possible to prepare a pharmaceutical composition aimed at regulating the administration dosis of orlistat. The pharmaceutical composition can be a type of tablet comprising a total of 120 mg or 60 mg of orlistat and which has a single or double groove, or powder for oral suspension provided in sachets or bicompartimented sachets. Both pharmaceutical compositions offer alternatively the possibility of administering variable doses of (−) tetrahydrolipstatin according to the patient's needs and/or the recommendation of the doctor consulted. Both compositions (tablets and powder for oral suspension) are easy to prepare from the mentioned premixture.

An object of this invention is to provide a pharmaceutical composition with dosage flexibility that makes it possible to easily adapt the dosis to the patient, minimising the side effects usually associated with the use of orlistat pellets in capsules (flatulence, steatorrhoea, etc). Negative effects that in many cases make it necessary for the patient to interrupt the treatment. Such dosage flexibility is absent from the capsules that comprise a fixed dosis of orlistat pellets.

Another object of this invention is to provide a simple method for industrial application that does not require any of the special equipment or plants used for industrially coating fairly unsoluble active ingredients. The method makes it possible to obtain a premixture with satisfactory pharmacotechnical characteristics for subsequently preparing tablets, and even other pharmaceutical forms for oral use.

DETAILED DESCRIPTION OF THE INVENTION

This invention relates to an oral pharmaceutical composition in the form of grooved tablets or sachets containing powder for suspension, comprising (−) tetrahydrolipstatin or orlistat and which allows the doctor or patient a more flexible dosis according to the particular situation and eating habits of each individual, as opposed to the commercially available capsule type pharmaceutical format, which only allows for the provision of the contained total of (−) tetrahydrolipstatin present in it, and not a fractioned dosis.

It has been proved on an experimental basis that it is possible to prepare tablets particularly, grooved tablets and sachets with powder for suspension, that comprise orlistat as described in the corresponding examples, without the need to use industrial operations prior to preparing the pharmaceutical composition which imply coating, pelletizing and/or extruding the active ingredient (orlistat) contained in said tablets and sachets.

To date the commercialised pharmaceutical forms (capsules) have been necessarily prepared following the convenient pelletizing, extrusion or coating of the active ingredient that they contain ((−) tetrahidrolipstatin).

Generally, as mentioned in the technical literature, including patent literature, the coating or pellitizing operations are characterized by the following aspects:

a) they are carried out on the active ingredient. They have been mentioned in various patents (U.S. Pat. No. 6,004,996);
b) they require specific equipment and industrial plants;
c) they imply various industrial stages.

Subsequently, starting with coated orlistat, or orlistat pellets, typical, normal equipment and plants, typical of the pharmaceutical industry, are used to prepare the pharmaceutical product for therapeutic application (capsules).

Whereas, the pharmaceutical composition of this invention is prepared by a simple industrial application method, that does not require any of the special equipment and plants for the industrial coating of fairly insoluble active ingredients. The method makes it possible to obtain a premixture of satisfactory pharmotechnical characteristics for subsequently preparing tablets and even other pharmaceutical forms for oral use Also, the method for preparing the premixture that comprises orlistat and other components is much quicker and more economical. It is possible to prepare, indistinctively, both tablets and powder for suspension from the premixture of this invention.

The pharmaceutical composition, which is the object of this invention, can contain 60 or 120 mg of orlistat, and it is fractionable.

The dosage flexibility provided by the pharmaceutical composition of this invention is new and particularly useful for doctors, because it makes it possible to easily regulate the dosis that each patient needs.

As far as the patient is concerned, it is economically convenient because with one single pharmaceutical composition of the grooved multidose tablet type, the patient can effect the dosis changes indicated by the doctor, and which the patient may need in order to minimise the side effects normally associated with the use of orlistat. This flexibility is not apparent in the single dose capsules available on the market.

So, for example:
1) With tablets comprising 120 mg of orlistat that are:
   a) Single grooved: The patient has 2 dosis options: 120 and 60 mg.
   b) Double grooved: The patient has 3 dosis options: 120, 80 and 40 mg.
2) With tablets comprising 60 mg of orlistat that are:
   a) Single grooved: The patient has 2 dosis options: 60 and 30 mg.
   b) Double grooved: The patient has 3 dosis options: 60-40 and 20 mg.
3) The sachets containing powder for oral suspension comprising 60 or 120 mg of orlistat also allow fractioning following the suspension in water. Also, such sachets can be compartmented, thereby helping to extend the dosage flexibility; for example, compartmented sachets containing 120 mg of orlistat, allow for 2 doses, each of 60 mg; compartmented sachets comprising 60 mg, allow for 2 doses, each 30 mg, or one 60 mg doses.

Surprisingly, it has been verified on an experimental basis that a specific premixture with orlistat in the form of a pure active ingredient (not pellets) makes it possible to simply prepare single- or multi-dose pharmaceutical compositions for oral use in the form of grooved tablets and also powder for suspension.

With this premixture, it is suffice to subsequently add the elements known in the state of the art to prepare each pharmaceutical form. For example: coating and colouring elements for the tablets, or suspension, colouring and flavouring agents for the oral suspension powder pharmaceutical format.

Far from being restrictive, the specific premixture that is preferred in this invention, contains the following:
  orlistat in the form of a pure active ingredient;
  a dilutent substance of the microchrystalline cellulose type;
  a substance for improving the flow of the powder mixture of the lactose monohydrate type;
  a surfactant substance of the sodium lauryl sulphate type;
  a substance for promoting the mixture of the components of the premixture of the colloidal anhydrous silica type;
  a lubricating substance of the sodium stearyl fumarate type;
  a substance for facilitating the break up and dispersion of the components of the final pharmaceutical composition in the presence of water of the carboxymethyl starch type;
components that afford the premixture suitable physical properties for the simple preparation of pharmaceutical compositions of oral use, by incorporating therein thickening, flavouring and colouring agents.

Preferably the dilutent substance of the microchrystalline cellulose type is selected from the group comprising microchrystalline cellulose, powder cellulose, modified cellulose, reticulated carboxymethylcellulose, calcium carboxymethylcellulose, crospovidone, hydroxymethyl cellulose, hydroxypropyl cellulose, coprocessed microchrystalline cellulose.

Preferably the substance for improving the flow of the powder mixture of the lactose monohydrate type is selected from the group comprising lactose, lactose monohydrate, coprocessed lactose.

Preferably the surfactant substance of the sodium lauryl sulphate type is selected from the group comprising sodium lauryl sulphate, docusate sodium.

Preferably the substance for promoting the mixture of the components of the premixture of the colloidal anhydrous silica type is selected from the group comprising colloidal anhydrous silica, hydrophobic colloidal silica.

Preferably the substance for facilitating the break up and dispersion of the components of the final pharmaceutical composition in the presence of water, of the carboxymethyl starch type is selected from the group comprising carboxymethyl starch, starch and modified starch.

Preferably the lubricating substance of the sodium stearyl fumarate type is selected from the group comprising sodium stearyl fumarate, magnesium stearate, calcium stearate, zinc stearate, stearic acid.

Preferably, in addition to orlistat in the form of a pure active ingredient, the premixture also comprises:
  between approximately 27 and 47% by weight of the total premixture of microchrystalline cellulose;
  between approximately 30 and 50% by weight of the total premixture of lactose monohydrate;
  between approximately 0.5 and 3% by weight of the total premixture of sodium lauryl sulphate;
  between approximately 0.5 and 3% by weight of the total premixture of colloidal anhydrous silica;
  between approximately 1 and 4% by weight of the total premixture of carboxymethyl starch;
  between approximately 0.5 and 3% by weight of the total premixture of sodium stearyl fumarate.

More preferably, in addition to orlistat in the form of a pure active ingredient, the premixture also comprises:
  approximately 37.5% by weight of the total of the premixture of microchrystalline cellulose;
  approximately 40.75% by weight of the total of the premixture of lactose monohydrate;

approximately 1.5% by weight of the total of the premixture of sodium lauryl sulphate;

approximately 1.25% by weight of the total of the premixture of colloidal anhydrous silica;

approximately 2.5% by weight of the total of the premixture of carboxymethyl starch;

approximately 1.5% of the total of the premixture of sodium stearyl fumarate.

In addition to the premixture, the pharmaceutical compositions also comprise thickening, flavouring and preserving agents, sweetening agents like sodium saccharin, and the necessary colouring agents such as quinoline yellow and S green; and coating agents.

The following essences can be used as flavouring agents: mint, cherry or aniseed, vanilla, apple and lemon.

Each component in the above-mentioned mixture of solids is widely known in the field of pharmaceutical technology for its characteristic properties, such as dilutent, bonding, disintegragion, surfactant, etc. However, as a whole the mixture provides novelty and practical advantage as it results in a mixture of pure orlistat that has suitable and convenient physical properties for preparing the claimed oral pharmaceutical compositions.

The invention also relates to a process for preparing compositions comprising the premixture of pure orlistat. The preparation of the premixture requires previously sieving each component, preferably through a mesh of 813 micra; the microchrystalline cellulose, sodium lauryl sulphate, pure orlistat, spray-dried lactose, colloidal anhydrous silica and carboxymethyl starch, and mixing them in a suitable mixer in an environment with a relative humidity level below 40% for 30 to 60 minutes. Sieving the sodium stearyl fumarate through a 813 micra mesh and adding it to the mixer together with the other components. Mix for a minimum of 5 minutes to obtain the premixture, where the physical behaviour of the latter is virtually absent from the characteristic unctuousity of pure orlistat. Preferably, the premixture is dry prepared, in an environment with a relative humidity level below 40% and at a temperature below 35° C.

Finally the premixture can be kept in an air-tight container until the respective pharmaceutical composition is prepared later.

By means of the composition of the premixture, it is possible to prepare tablets and powder for oral suspension.

In the case of the tablets, the premixture in bulk comprising the pure orlistat is compressed in a suitable compressor so as to obtain the tablets, and subsequently the tablets are coated with a coating suspension of the desired colour.

In the case of the powder for oral suspension, flavouring and sweetening agents, sieved previously, are added to the premixture, and sachet doses are prepared.

It has also been determined that the following conditions are preferably:

1) the pure orlistat content is prefereably less than 20% by weight of the total weight of the premixture, and most preferably between 12 and 17%;

2) the operations are preferably carried out at a maximum temperature of 35° C., most preferably less than 30° C.;

3) the mixture of components are preferably prepared in a dry environment. As the presence of water would require subsequent drying, which would affect the stability of the active ingredient and the physical characteristics of the premixture.

The method for preparing the compositions of this invention offers the following advantages over other known methods:

1) it uses orlistat in the form of a pure active ingredient;

2) it overcomes the technical drawbacks caused by the low melting point and the adhesivity of orlistat for preparing oral compositions;

3) it is more economical than other alternatives that require previously transforming the active ingredient into pellets, or coating it, and includes fewer stages and is not so expensive;

4) on an industrial level it does not require special equipment of plants for pelleting, extruding or coating the orlistat;

5) the pharmaceutical compositions are prepared using simple equipment and plants that already exist throughout the pharmaceutical industry;

6) all the operations are carried out at temperatures below the melting point of orlistat, thereby avoiding its partial hydrolysis and possible heat degradation;

7) for the patient, the composition prepared from the premixture that comprises orlistat, offers greater dosage flexibility than the capsules comprising orlistat pellets designed for one single dose.

To summarise, with the above-mentioned premixture it is possible to prepare pharmaceutical compositions for oral use, with convenient dosage flexibility in a technologically simple format such as single dose or multidose powder for oral suspension, or, grooved tablets comprising 60 or 120 mg of pure orlistat in the their composition. These compositions fulfill the necessary requirements of content uniformity and stability. Preparing capsules with the premixture that comprises orlistat is also viable; but, since it lacks dosage flexibility for the patient, it is less interesting.

The following examples, far from being restrictive, illustrate how to put this invention into practice.

EXAMPLES

Example 1

Preparation of Premixture for Preparing Pharmaceutical Compositions Comprising 60 Mg of Orlistat Per Unit Stages:

A) Sieve the following components in Quadro Comill Mod 197 S Conical Sieve Mill or the like, using 813 micra mesh:

| | |
|---|---|
| Microchrystalline cellulose | 375.00 g |
| Sodium Lauryl Sulphate | 15.00 g |
| Orlistat | 150.00 g |
| Lactose monohydrate | 407.50 g |
| Colloidal Anhydrous Silica | 12.50 g |
| Carboxymethyl starch | 25.00 g |

Add to Erweka AMD motor type 5V1M Rotating Sieve with Type FGS accessory and equivalent Conical Mixer.

B) Mix for 30 minutes.

C) Sieve under identical conditions and add to Conical Mixer:

| | |
|---|---|
| Sodium stearyl fumarate (PRUV) | 15.00 g |

D) Mix for 5 minutes.

E) Keep the mixture in an air-tight container.

The above-mentioned amount of orlistat (if necessary) must be adjusted according to the title of the active ingredient.

1 kg of premixture is obtained.

The premixture in bulk (1 kg) that is obtained can be applied indistinctively to preparing grooved, coated tablets or powder for oral suspension.

Approximately 2500 units can be prepared, with each one comprising 60 mg of orlistat.

Example 2

Preparation of Grooved, Coated Tablets Comprising 60 Mg of Orlistat

Stages:

A) Direct Compression

The bulk mixture of orlistat and other components prepared in Example 1) was compressed in a Riva Piccola Model B-2 rotary compressor fitted with 6 punching tools and with Autoset HI TECH or the like, to a theoretical weight of 400 mg.

Tablets with the following characteristics were obtained:
a) Weight:
   Average weight: 400 mg (390-410 mg)
   Measuring equipment: Mettler Toledo AB 204-S Scales with LC P45 Printer
b) Hardness: 15-25 Sc
Measuring equipment: ERWEKA Type TBH 30 MD durometer
c) Brittleness: less than 0.5%
Measuring equipment: Pharmaceutical brittleness equipment
d) Disintegration: less than 10 minutes in water at 37° C.
Measuring equipment: AVIC Disintegrating equipment
   Conditioning the sieved tablets in suitable containers.

B) Coating

1) Preparation of the Colour Coating Suspension

The following was added to a stainless steel container of suitable capacity and fitted with Heidolph type RZR 1 Mechanical Stirrer, or the like:

| Purified water | 330.00 g |
|---|---|

Start stirring at a speed that ensures the formation of a vortex.

Add the following, and stir continuously inside the vortex at a speed that minimises floating powder and ensures dispersion:

| Lactose monohydrate | 18.00 g |
|---|---|
| Hypromellose | 18.00 g |
| Triacetine | 4.50 g |
| Titanium dioxide | 4.50 g |

Maintain energetic stirring for 5 minutes.

Reduce stirring speed until vortex is removed.

Maintain stirring until dispersion is complete.

The suspension must be used within 24 hours of being prepared.

2) Nuclei Coating

Then coat the nuclei in Rama Cota model NR 18 pan coating system, or the like, using Binks 460 Pistols.

Apply the colour coating suspension over the tablets.

Throughout the operation, the temperature of the nuclei should not exceed 35° C.

Condition the tablets in suitable containers with a polyethylene bag.

C) Conditioning:

Place the tablets in the following type of blister packs:

PVC 250 micra/PVDC 60 g/m$^2$—Aluminium.

Approximately 2500 tablets are obtained, each comprising 60 mg of orlistat.

Example 3

Preparation of Powder for Oral Suspension in Single Dose Sachets Containing 60 Mg of Orlistat Per Unit Stages:

1) Prepare a premixture or orlistat in bulk according to Example 1, that comprises the following components:

| Microchrystalline cellulose | 37.00 g |
|---|---|
| Sodium Lauryl Sulphate | 15.00 g |
| Orlistat | 150.00 g |
| Lactose monohydrate | 407.50 g |
| Colloidal Anhydrous Silica | 12.50 g |
| Carboxymethyl starch | 25.00 g |
| Sodium stearyl fumarate | 15.00 g |

2) Sieve separately in a Quadro Comill 197 S Conical Sieve Mill, using a 813 micra mesh:

| Sodium Saccharin | 125.00 g |
|---|---|
| Sodium Alginate | 625.00 g |
| Apple Essence | 75.00 g |
| Lime Essence | 81.75 g |
| Quinoline Yellow | 2.50 g |
| Green S | 0.125 g |
| Granular Mannitol | 6840.625 g |

Add both powder mixtures from stages 1 and 2 to a Erweka AMD motor type 5V1M Rotating Sieve with Type FGS accessory and Conical Mixer, or the like.

3) Mix for 20 minutes.

4) Proportioning and Packaging of Single Dose Sachets:

In a humid environment at an appropriate temperature, Rovema type sachets or the like were proportioned in a proportioning machine, using the following material:

Foil 83 g/m$^2$+Pe 40µ chrystal (Triple Foil)

Then packaging is carried out according to the following specifications:

Theoretical filling weight: 3500 mg

Maximum tolerated individual weight: 3675 mg

Minimum tolerated individual weight: 3325 mg

Approximately 2500 single dose sachets were obtained for oral suspension, each comprising 60 mg of orlistat.

Example 4

Preparation of Premixture for Preparing a Pharmaceutical Form Comprising 120 G. of Orlistat Per Unit The premixture was prepared according to Example 1.
The amount of orlistat was corrected according to the title.
1 kg of premixture was obtained.
The premixture obtained can be applied indistinctively to preparing grooved, coated tablets or powder for suspension.
Approximately 1250 units were obtained, each containing 120 mg of orlistat.

Example 5

Preparation of Grooved, Coated Tablets Comprising 120 mg of Orlistat

Stages:
1) Direct Compression:
The premixture of orlistat and other components according to Examples 4 and 1 was compressed, in a Riva Piccola Model B-2 rotary compressor fitted with 6 punching elements and with Autoset HI TECH or the like, to a theoretical weight of 800 mg.
Grooved tablets were obtained with the following parameters:
a) Weight:
   Average Weight: 800 mg (780-820 mg)
   Measuring equipment: Mettler Toledo AB 204-S Scales with LC P4 Printer
b) Hardness: 22-28 Sc
   Measuring equipment: ERWEKA Type TBH 30 MD Durometer
c) Brittleness: less than 0.5%
   Measuring equipment: Pharmaceutical Brittleness Equipment
d) Disintegration: less than 10 minutes in water at 37° C.
   Measuring equipment: AVIC Disintegrating equipment.
The sieved tablets were conditioned in suitable containers with a polyethylene bag.
2) Preparation of Colour Coating Suspension:
The following were added to stainless steel containers of suitable capacity and fitted with Heidolph type RZR 1 Mechanical Stirrer or the like:
Purified Water 330.00 g
The following were added while being stirred at a speed that ensures the formation of a vortex so to reduce floating powder and ensure its even dispersion:

| | |
|---|---|
| Lactose monohydrate | 18.00 g |
| Hypromellose | 18.00 g |
| Triacetina | 4.50 g |
| Titanium Dioxide | 4.50 g |

Energetic stirring was maintained for 5 minutes. Then the stirring was reduced and maintained until all was dispersed. The coating suspension was used within 24 hours of being prepared.
3) Coating the Tablets Obtained:
The coating was carried out in a pan coating system (Rama Cota model NR 18) using Binks 460 Pistols. The tablets to be covered were prepared and kept at a temperature below 35° C.

4) The coated tablets obtained were packaged in blisters made of 250 micra PVC foil/PVDC 60 g/m² Aluminium.
Approximately 1250 grooved tablets were obtained with an average weight of 800 mg and a content of 120 mg of orlistat.

Assessment of Dissolution Profile
The dissolution profiles were determined between the grooved tablets obtained containing 120 mg of orlistat (E-007) and a batch of capsules used as a reference (Xenical capsules Batch M1255—Due Date August 2008). The determinations were made according to the guide entitled, "Dissolution Methods for Drug Products"—FDA.
Materials and Methods:
Apparatus: 2 (blades, USP); 75 rpm
Medium Buffer pH=6.0; 900 ml
Sampling Times: 10, 20, 30, 45 and 60 minutes
Sampling volume: 10 ml (with resting medium)
Quantification: HPLC
Results:

| Orlistat 120 mg CoR E-007 | | |
|---|---|---|
| Time (minutes) | % dissolved | CV % |
| 10 | 61 | 2.3 |
| 20 | 77 | 2.0 |
| 30 | 84 | 1.9 |
| 45 | 90 | 1.6 |
| 60 | 93 | 1.3 |

| Xenical Cps L-M1255 | | |
|---|---|---|
| Time (minutes) | % dissolved | CV % |
| 10 | 48 | 7.1 |
| 20 | 72 | 2.8 |
| 30 | 82 | 1.9 |
| 45 | 90 | 1.8 |
| 60 | 94 | 1.9 |

Example 6

Preparation of Powder for Oral Suspension in Single Dose Sachets Each Comprising 120 mg of Orlistat Stages:
1) A total of 8.750 kg of the mixture of orlistat and the other components according to Example 3 was prepared, containing 150 g of orlistat.
2) Proportioning and Packaging in single dose sachets: In controlled temperature and humidity environments, the following material was proportioned in Proportioning Machine in sachets (Rovema):
Foil 86 g/m²+Pe 40μ chrystal (Triple Foil)
A total of 1250 single dose sachets were obtained, each containing 120 mg of orlistat.

Example 7

Preparation of Powder for Oral Suspension in Bicompartmented Sachets

They were prepared in a similar way to Examples 3 and 6, each containing a total of 60 and 120 mg of orlistat.

In both cases the powder mixture obtained was proportioned and packaged in bicompartmented sachets made from the same material as mentioned in each example. The bicompartmented sachets obtained offer respectively the possibility of choosing to take either a 60 or 30 mg dose, or a 120 or 60 mg dose of orlistat.

Example 8

Method according to Examples 3 and 6 wherein the flavouring agents mentioned in each case are replaced, and each single dose sachet comprises 39.92 mg of sucralose, 50 mg of strawberry essence, 37.5 mg of peppermint essence and 15 mg of masking flavor.

Example 9

Method according to Examples 3 and 6 wherein the flavouring agents mentioned in each case are replaced, and each single dose sachet comprises 93.0 mg of chocolate essence; 199 mg of cream essence, and 307.8 mg of cocoa.

Example 10

Preparation of Multi-Dose Powder for Oral Suspension 35 g of powder mixture prepared according to Example 6 and with an equivalent content of 600 mg of orlistat, were packaged in a 300 ml capacity polypropylene bottle. When reconstituted subsequently with 250 ml of water and kept at a low temperature, it proved to have suitable pharmaceutical stability and convenient dosage flexibility. In that every 12.5 ml comprise the equivalent of 30 mg of orlistat.

Assays

A study was conducted with 55 patients of both sexes who had previously been receiving treatment with orlistat pellets in capsules for an average time of 8 months. The patients were treated subsequently, and according to each case, with doses of 120 and 240 mg/day of pure orlistat tablets. The results indicated that 63% of the patients had equal tolerance to the treatment with orlistat capsules, but 37% showed greater tolerance with orlistat tablets. Also 63% of the patients preferred the tablets to the capsules.

The principles, the preferred types and the modus operandi of this invention have been described in the specification herein. However, it is not to be considerd that the invention that claims protection herein, is limited to the particular formats described, as they have to be considered to be illustrative and not restrictive. Variations and alterations can be made by those skilled in the art, without departing from the spirit of this invention.

The invention claimed is:

1. Pharmaceutical composition with anti-obesity activity that acts peripherally, characterized in that it comprises a low adhesion premixture made up of:
   orlistat in the form of pure, non-pelletized, active ingredient, where the orlistat content in the premixture is less than 20% of the total weight of the mass;
   a diluent substance selected from the group consisting of microcrystalline cellulose, powder cellulose, modified celluose, reticulated carboxymethyl cellulose, calcium carboxymethyl cellulose, crospovidone, hydroxymethyl cellulose, hydroxypropyl cellulose and coprocessed microcrystalline cellulose;
   a substance for improving the flow of the powder mixture selected from the group consisting of lactose, lactose monohydrate, and coprocessed lactose;
   a surfactant substance selected from the group consisting of sodium lauryl sulphate and docusate sodium;
   a substance for promoting the mixture of the components of the premixture selected from the group consisting of colloidal anhydrous silica and hydrophobic colloidal silica;
   a lubricating substance selected from the group consisting of sodium stearyl fumarate, magnesium stearate, calcium stearate, zinc stearate and stearic acid;
   a substance to facilitate the breakdown and dispersion of the components of the final pharmaceutical composition in the presence of water selected from the group consisting of carboxymethyl starch, starch and modified starch.

2. Pharmaceutical composition according to claim 1, in the form of grooved tablets or powder for suspension.

3. Pharmaceutical composition according to claim 1, comprising:
   orlistat in the form of pure, non pelletized, active ingredient;
   microcrystalline cellulose;
   lactose monohydrate;
   sodium lauryl sulphate;
   colloidal anhydrous silica;
   carboxymethyl starch; and
   sodium stearyl fumarate.

4. Pharmaceutical composition according to claim 3, wherein in addition to orlistat in the form of pure, non pelletized, active ingredient the premixture also comprises:
   between approximately 27 and 47% by weight of the total of the premixture of microcrystalline cellulose;
   between approximately 30 and 50% by weight of the total of the premixture of lactose monohydrate;
   between approximately 0.5 and 3% by weight of the total of the premixture of sodium lauryl sulphate;
   between approximately 0.5 and 3% by weight of the total of the premixture of colloidal anhydrous silica;
   between approximately 1 and 4% by weight of the total of the premixture of carboxymethyl starch;
   between approximately 0.5 and 3% of the total of the premixture of sodium stearyl fumarate.

5. Pharmaceutical composition according to claim 4, wherein in addition to pure, non pelletized, orlistat the premixture also comprises:
   approximately 37.5% by weight of the total of the premixture of microcrystalline cellulose;
   approximately 40.75% by weight of the total of the premixture of lactose monohydrate;
   approximately 1.5% by weight of the total of the premixture of sodium lauryl sulphate;
   approximately 1.25% by weight of the total of the premixture of colloidal anhydrous silica;
   approximately 2.5% by weight of the total of the premixture of carboxymethyl starch; and
   approximately 1.5% of the total of the premixture of sodium stearyl fumarate.

6. Pharmaceutical composition according to claim 1, comprising in addition to the premixture, a thickening and suspension agent selected from the group consisting of sodium alginate, xanthan gum, gum arabic, hydroxypropyl cellulose, hydroxymethyl cellulose, guar gum, methylcellulose, mannitol cellulose derivatives as dilutent, flavouring agents selected from saccharine, cyclamate, acesulfame potassium, sucralose, debitter, taumatine, sorbitol, lactitol, apple essence, lime essence, lemon essence, citric acid, chocolate and cream essence; and colouring agents selected from quinoline yellow, greens, brilliant blue and allura red.

7. Pharmaceutical composition according to claim 1, wherein the orlistat content in the premixture is between 12 and 17% of the total weight of the mass.

8. Pharmaceutical composition according to claim 1, in the form of grooved tablets comprising 120 mg of orlistat.

9. Pharmaceutical composition according to claim 1, in the form of grooved tablets comprising 60 mg of orlistat.

10. Pharmaceutical composition according to claim 1, in the form of double groove tablets comprising 120 mg of orlistat.

11. Pharmaceutical composition according to claim 1, in the form of double groove tablets comprising 60 mg of orlistat.

12. Pharmaceutical composition according to claim 1, in the form of powder for extemporaneous preparation by dispersion in water and wherein the composition comprises 60 mg of orlistat per unit dose.

13. Pharmaceutical composition according to claim 1, in the form of powder for extemporaneous preparation by dispersion in water of a suspension and wherein the composition comprises 120 mg of orlistat per unit dose.

14. Pharmaceutical composition according to claim 1, wherein the powder composition for suspension is packaged in aluminium-aluminium bicompartmented sachets and offer greater dosage flexibility.

15. The multi-dose pharmaceutical composition according to claim 1, in the form of powder for preparation by dispersion in water of a suspension comprising multiple dose units containing 60 mg of orlistat.

16. Method for preparing a premixture composition useful in the composition according to claim 1 comprising:
sieving through a 813 micra mesh and adding to a suitable mixer: microchrystalline cellulose, sodium lauryl sulphate, orlistat, spray-dried lactose, colloidal anhydrous silica and carboxymethyl starch,
mixing for a minimum of 30 minutes,
sieving through a 813 micra mesh the sodium stearyl fumarate and adding to the mixer said microchrystalline cellulose, sodium lauryl sulphate, orlistat, spray-dried lactose, colloidal anhydrous silica and carboxymethyl starch, and
mixing for a minimum of 5 minutes;
to obtain a premixture with a physical behaviour that is virtually absent from the characteristic spreadability of pure orlistat.

17. Method according to claim 16, wherein said premixture is dry prepared in an environment with relative humidity at a level below 40% and at a temperature below 35° C.

18. Method of claim 16 wherein said premixture is obtained by compressing directly into a tablet; and subsequently coating said tablet.

19. Method of claim 16, further comprising adding flavouring, thickening, colouring agents and essences to said premixture in an environment with relative humidity at a level below 40% and at a temperature below 35° C.

* * * * *